(12) United States Patent
Larsen et al.

(10) Patent No.: US 11,245,990 B2
(45) Date of Patent: *Feb. 8, 2022

(54) BODY TEMPERATURE HEARING AID

(71) Applicant: Oticon A/S, Smørum (DK)

(72) Inventors: Mathias Bruun Larsen, Smørum (DK); Mikkel Nielsen, Smørum (DK); Kenneth Rueskov Møller, Smørum (DK); Ole Andersen, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/999,659

(22) Filed: Aug. 21, 2020

(65) Prior Publication Data
US 2020/0382877 A1   Dec. 3, 2020

Related U.S. Application Data

(63) Continuation of application No. 16/425,486, filed on May 29, 2019, now Pat. No. 10,779,090.

(30) Foreign Application Priority Data

May 30, 2018   (EP) ..................... 18175214

(51) Int. Cl.
*H04R 25/02*   (2006.01)
*H04R 25/00*   (2006.01)
*A61B 5/01*   (2006.01)

(52) U.S. Cl.
CPC ............. *H04R 25/02* (2013.01); *A61B 5/01* (2013.01); *H04R 25/70* (2013.01); *H04R 25/554* (2013.01); *H04R 25/604* (2013.01); *H04R 25/652* (2013.01)

(58) Field of Classification Search
CPC ...... H04R 25/02; H04R 25/70; H04R 25/652; H04R 25/604; H04R 25/554; H04R 25/305; H04R 2225/61; H04R 1/1041; H04R 1/1016; H04R 25/552; A61B 5/01; A61B 5/1118; A61B 5/6817; A61B 2562/0271; A61B 2562/0219
See application file for complete search history.

(56) References Cited

U.S. PATENT DOCUMENTS

| | | | | |
|---|---|---|---|---|
| 7,453,366 B2 * | 11/2008 | Grilliot | ................ | G08B 3/10 340/584 |
| 8,652,040 B2 * | 2/2014 | LeBoeuf | ............. | A61B 5/0022 600/301 |
| 9,838,771 B1 * | 12/2017 | Masaki | ............... | G01R 33/072 |
| 2006/0045304 A1 * | 3/2006 | Lee | ...................... | H04R 1/1041 381/384 |
| 2009/0221888 A1 * | 9/2009 | Wijesiriwardana | .. | A61B 5/6817 600/324 |

(Continued)

FOREIGN PATENT DOCUMENTS

| | | |
|---|---|---|
| DE | 202010016226 U1 | 3/2011 |
| JP | 2010-236897 A | 10/2010 |
| WO | WO 2014/071412 A1 | 5/2014 |

*Primary Examiner* — Oyesola C Ojo
(74) *Attorney, Agent, or Firm* — Birch, Stewart, Kolasch & Birch, LLP

(57) ABSTRACT

A hearing aid device including sensors are disclosed. Specifically, a hearing aid with a temperature sensor and a reference sensor. Also disclosed is a method for estimating body core temperature.

13 Claims, 6 Drawing Sheets

(56) References Cited

U.S. PATENT DOCUMENTS

| | | | |
|---|---|---|---|
| 2014/0169400 A1* | 6/2014 | Baarman | A61B 5/01 374/45 |
| 2014/0321682 A1* | 10/2014 | Kofod-Hansen | H04R 25/30 381/315 |
| 2015/0182135 A1* | 7/2015 | Ma | A61B 5/6824 600/301 |
| 2015/0215719 A1* | 7/2015 | Turgul | H04R 1/1091 381/58 |
| 2015/0230036 A1* | 8/2015 | Pedersen | H04R 25/305 381/330 |
| 2016/0057547 A1* | 2/2016 | Burger | H04R 25/00 381/315 |
| 2016/0133151 A1* | 5/2016 | O'Dowd | G06F 3/015 434/236 |
| 2018/0228435 A1* | 8/2018 | LeBoeuf | A61B 5/14552 |
| 2018/0256106 A1* | 9/2018 | Rogers | A61B 5/7246 |
| 2019/0117155 A1* | 4/2019 | Cross | G01K 13/20 |

* cited by examiner

BODY TEMPERATURE HEARING AID

CROSS-REFERENCE TO RELATED APPLICATIONS

This application is a Continuation of co-pending application Ser. No. 16/425,486, filed on May 29, 2019, which claims priority under 35 U.S.C. § 119(a) to application No. 18175214.8, filed in Europe on May 30, 2018, all of which are hereby expressly incorporated by reference into the present application.

The present disclosure relates to hearing aids. More particularly, the disclosure relates to methods and systems in and for hearing aid device, where the body temperature of the person wearing the hearing aid is measured. Further, the present disclosure relates to methods for compensating body temperature measurements obtained via hearing aids.

Hearing aids may be provided in different configurations, such as commonly denoted In-the-Ear, Receiver-In-the-Ear, Behind-the-Ear and so forth.

In-the-ear hearing aid devices (ITE) usually comprise an exterior housing (of an in-the-ear unit thereof) and an electro-acoustic output transducer arranged therein. Receiver-In-the-Ear (RITE) hearing aid devices usually comprise an exterior housing configured to be positioned behind the ear of the user, with an electro-acoustic output transducer arranged in a separate housing configured to be placed at least partly in the ear canal of the user. Behind-the-Ear hearing aid devices (BTE) usually comprise an exterior housing configured to be positioned behind the ear of the user, with an electro-acoustic output transducer arranged in the same housing and be configured to be connected to a hollow tube arranged for guiding acoustic sound from the output transducer to the ear canal of the user.

The electro-acoustic output transducer is often termed a receiver and is configured to convert an electric audio signal into an acoustic sound signal. The electric audio signal may be provided by a sound processor. The sound processor may receive an electric audio input signal and process the electric audio input signal to generate a processed electric audio signal to be fed to the output transducer. The sound processor may process the sound so as to compensate for a specific hearing loss of the intended user.

The sound processor may be provided in a behind-the-ear unit of the hearing aid or for the ITE hearing aid in the housing configured to be positioned in or at the ear canal. The electric audio input signal may be received from an electro-acoustic input transducer. Alternatively, or in combination herewith, the electric audio input signal may be received wirelessly, e.g. via an RF radio channel, such as via a Bluetooth connection or the like, or other types of wireless signals, such as telecoil, inductive systems or the like. The electro-acoustic input transducer may be provided in the in-the-ear unit or may be provided in the BTE unit. The electro-acoustic input transducer is called microphone and converts an acoustic sound signal into an electric audio signal.

In RITE hearing aids, the sound processor is typically arranged in the BTE unit and is connected to the electro-acoustic output transducer (and the electro-acoustic input transducer) by way of electrically conducting wires arranged in a coupling element (connection tube) that mechanically connects the in-the-ear unit to the behind-the-ear unit.

When people wear a hearing aid, the device is usually placed in close contact with the head of the user, and if a temperature sensor is included and arranged as close to the ear drum as possible, within the hearing aid housing or the in-the-ear-canal housing having the receiver as well, it is possible to obtain a measurement of the temperature in the ear canal, which may be used as an estimate of the core temperature of the user. This, first, temperature sensor is thus utilized to establish an estimate of the core temperature of the person wearing the hearing instrument from inside the ear(canal) using a sensor attached to the receiver. In addition to the usual measurement insecurities, other factors may degrade the estimate.

Therefore, there is a need to provide a solution that at least provides an improved estimate of the body temperature of the person wearing the hearing aid, and at least alleviates some of the above-mentioned problems. The present disclosure provides at least an alternative to the prior art.

In a first aspect, the present disclosure provides a hearing aid having a first housing, the first housing being configured to be positioned at least partly in the ear canal of the user. The hearing aid may further comprise a first temperature sensor arranged in the first housing, and an output transducer arranged in the first housing. The hearing aid may further comprise a temperature processor configured to process signals from the first temperature sensor, and a reference temperature sensor in communication with the temperature processor. By having such two temperature sensors, during use preferably arranged with as large a distance between them as possible, it becomes possible to improve the estimate of the core temperature of the user. The hearing aid may further comprise that the temperature processor may be configured to estimate, based on both the first measure body temperature of the user and the reference temperature, a core body temperature of the user. Further, this configuration allows for an improved comfort of the user as it does not require a closed environment in the ear canal. In contrast, it is possible to implement the hearing aid as what is sometimes referred to as an open system where ambient sound is allowed to enter the ear canal and reach the ear drum and air is also allowed to escape the inner part of the ear canal.

The first housing may further comprise an output transducer, wherein the processor may then be further configured to provide the estimate based on output transducer activity. This is advantageous in that it becomes possible to compensate the temperature estimate by compensating for the local heating of the temperature sensor which originates from the heat development in the output transducer. The information may be obtained from the processor processing the incoming sound and generating the compensated sound signal. This processor may in some instances be implemented in the same, physical, processor as the mentioned temperature processor.

The first housing may comprise a first end and an opposite second end, wherein the first temperature sensor is arranged in the second end of the first housing and the output transducer is arranged at an extreme of the second end. The first housing may be an elongated housing where the output transducer is positioned at one end, e.g. at an extreme end or distal end, and the temperature sensor is then positioned in the same housing. There may be included some temperature barriers so as to reduce the transfer of heat from the output transducer to the temperature sensor. The first housing may be configured to receive a dome so that when the user uses the hearing aid, the first housing is more comfortable to wear.

The hearing aid may further comprise a second housing, the reference temperature sensor may then be arranged in the second housing. This could for instance be a housing configured to be positioned behind the ear of the user. In other instances, the second housing may be configured to be positioned in the concha of the user and/or the fossa triangularis. The second housing may be mechanically connected to the first housing, e.g. via a connecting member. A connecting member may include one or more electrically conducting members, which may be used for carrying, i.e. sending, signals to/from one of the houses to the other. Such a communication may be one-way or both ways. The first housing, the connecting member and the second housing may enable a hearing aid to be configured as a so-called receiver-in-the-ear hearing aid. In such a hearing aid, the first housing is configured to be located in the ear canal of the user, the second housing configured to be located behind the pinna of the user and the connecting member to act as a connecting between the two housings. Other configurations are possible, such as mentioned the second housing in the helix, anti-helix or elsewhere in/at the pinna.

An RF antenna may be included in the hearing aid. The RF antenna could be arranged in the housing to be positioned behind the ear of the user. The RF antenna could be arranged in an element configured to connect an in-the-ear housing with a behind-the-ear housing. The RF antenna could be arranged so as to be positioned in the concha while the user wears the hearing aid.

The reference temperature sensor may be arranged in an external device in wired or wireless communication with the temperature processor. This could allow for a more accurate ambient temperature estimate, as such as measurement could be less influenced by the body heat of the user.

An inductive communication system may be included in the hearing aid. Such an inductive communication system may be used for communicating wirelessly between hearing aids positioned at opposite ears of a user, as inductive communication have shown to be energy efficient when communicating through the head of the user, whereas high frequency communication have proved to be less efficient.

The external device may be a telephone device or an auxiliary device having a microphone array. This could be beneficial as such devices are often already carried by hearing aid users. Further, if a telephone, such as a smartphone, is used, an user interface thereof may be used to provide the user with health related information, e.g. information based on estimates of body core temperature and/or other body related data.

The hearing aid may further comprise a motion sensor configured to provide an indication of movement of the hearing aid, and the temperature processor includes movement of the hearing aid as a measure of movement of the user when estimating the core body temperature of the user. Motion/movement of the user could influence the user, i.e. if the user is engaged in physical activity, both ear canal temperature and external temperature may be influenced by increased body temperature. Also, local cooling of the hearing aid may occur as local increased moisture at the ear may decrease due to the user moving around.

The hearing aid may further comprise a secondary sensor configured to obtain a measure indicative of wind at the hearing aid, and the temperature processor includes wind measure at the hearing aid when estimating the core body temperature of the user. It could be beneficial to include additional sensors for, in total, obtaining several physical measures, all of which could help improve estimate of the core body temperature. As mentioned, wind could decrease temperature at the ear, resulting in a lowered reference temperature, which again could change the estimate of the body core temperature.

In a second aspect, the present disclosure relates to a method of obtaining an estimate of the core body temperature of a user. The user could be wearing a hearing aid according to the first aspect. The method may include a step of arranging the first housing in or at the ear canal of the user so that the first temperature sensor is in the ear canal of the user, the reference temperature sensor being arranged, at least partly, outside the ear canal of the user. As mentioned, the reference temperature sensor may be external to the hearing aid, or may be external to just the first housing, e.g. positioned in a behind-the-ear housing while the first temperature sensor may, still, be positioned as close as possible to the ear drum of the user. Physically it is not always possible, or desirable, to place the first temperature sensor in direct contact with the ear drum. The method may include a step of obtaining from the first temperature sensor a first measure of body temperature of the user. The method may include a step of obtaining a reference temperature from the reference temperature sensor. The method may include a step of estimating, based on both the first measure body temperature of the user and the reference temperature, a core body temperature of the user. The estimate may be established by including a number of prior measurements. This could be done to reduce the risk of basing the estimate, entirely, on spikes/extremes in the measurement.

The hearing aid used in the method according to the second aspect may include a first housing configured to be positioned at least partly in the ear canal of the user, the first housing including a first temperature sensor, a temperature processor configured to process signals from the first temperature sensor, a reference temperature sensor in communication with the temperature processor.

The first housing may further comprise an output transducer, and the method according to the second aspect may comprise a step of including output transducer activity when estimating the core body temperature.

The reference temperature sensor may be arranged in an external device in wired or wireless communication with the temperature processor, and the method according to the second aspect may comprise a step of communicating the reference temperature wired or wirelessly from the external device to the temperature sensor.

The hearing aid may further comprise a motion sensor configured to provide an indication of movement of the hearing aid, and the method according to the second aspect may comprise a step of obtaining data relating to movement of the hearing aid as a measure of movement of the user, and the step of estimating the core body temperature of the user includes the data relating to movement of the hearing aid.

The hearing aid may further comprise a secondary sensor configured to obtain a measure indicative of wind at the hearing aid, and the method according to the second aspect may comprise a step of obtaining data relating to wind measure at the hearing aid, and the step of estimating the core body temperature of the user includes the data relating to wind measure.

The hearing aid according to the first aspect may be included in a binaural hearing aid system where a hearing aid is arranged at respective left and right ear of a user, and the two hearing aids are configured to exchange data wirelessly or wired. This exchange could include sending sensor data from one hearing aid to the other, either raw sensor data or processed data, i.e. data indicating situations determined based on data from the sensor or sensors. The two hearing aids of the binaural hearing aid system may be operated based on data from a sensor in each hearing aid, e.g. similar sensors arranged in each hearing aid, or, different sensor types, where the left hearing aid as one type of sensor, and the right hearing aid has a second type of sensor being different from the first type of sensor.

The method may also be adapted to operate on a binaural hearing aid system accordingly.

All features mentioned in relation to the first and second above may be combined where appropriate.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
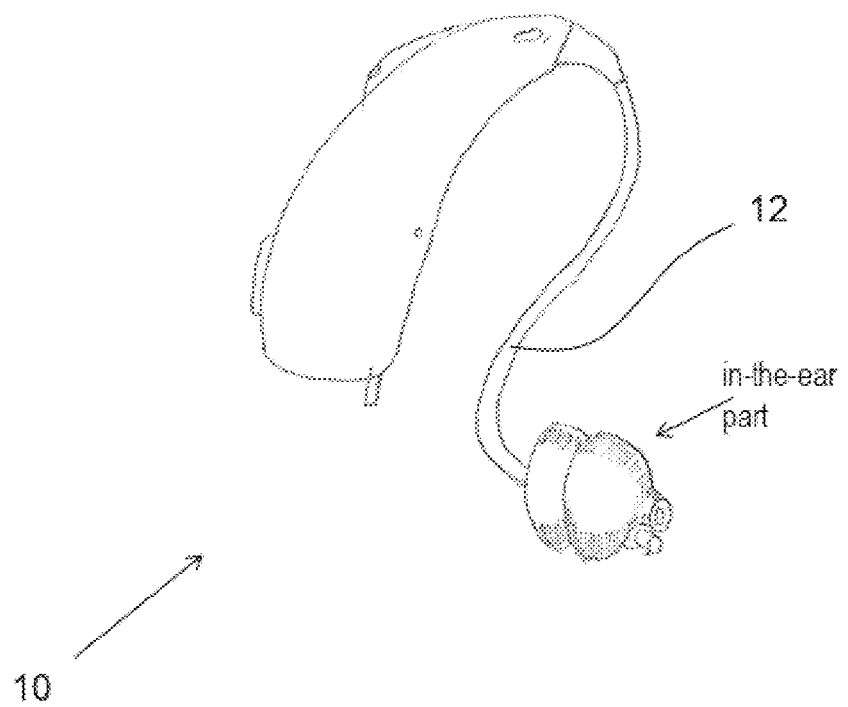
FIG. 1 schematically illustrates a hearing aid.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing aid device, or simply hearing aid, may be a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing aid device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing aid device is adapted to be worn in any known way. This may include i) arranging a unit of the hearing aid device behind the ear with a tube leading air-borne acoustic signals into the ear canal or with a receiver/loudspeaker arranged close to or in the ear canal such as in a Behind-the-Ear type hearing aid, and/or ii) arranging the hearing aid device entirely or partly in the pinna and/or in the ear canal of the user such as in a In-the-Ear type hearing aid or In-the-Canal/Completely-in-Canal type hearing aid, or iii) arranging a unit of the hearing aid device attached to a fixture implanted into the skull bone such as in Bone Anchored Hearing Aid or Cochlear Implant, or iv) arranging a unit of the hearing aid device as an entirely or partly implanted unit such as in Bone Anchored Hearing Aid or Cochlear Implant.

A "hearing system" refers to a system comprising one or two hearing aid devices, and a "binaural hearing system" refers to a system comprising two hearing aid devices where the devices are adapted to cooperatively provide audible signals to both of the user's ears. The hearing system or binaural hearing system may further include auxiliary device(s) that communicates with at least one hearing aid device, the auxiliary device affecting the operation of the hearing aid devices and/or benefitting from the functioning of the hearing aid devices. A wired or wireless communication link between the at least one hearing aid device and the auxiliary device is established that allows for exchanging information (e.g. control and status signals, possibly audio signals) between the at least one hearing aid device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing aid device. The remote control is adapted to control functionality and operation of the at least one hearing aid devices. The function of the remote control may be implemented in a SmartPhone or other electronic device, the SmartPhone/electronic device possibly running an application that controls functionality of the at least one hearing aid device.

In general, a hearing aid device includes i) an input unit such as a microphone for receiving an acoustic signal from a user's surroundings and providing a corresponding input audio signal, and/or ii) a receiving unit for electronically receiving an input audio signal. The hearing aid device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing aid devices, the output unit may include one or more output electrodes for providing the electric signals such as in a Cochlear Implant.

The present method for compensating an estimate of a core body temperature of a hearing aid wearer/user may be used in hearing aids having external stimulation of the ear of the user, i.e. in BTE-, ITE- and RITE-style hearing aids, but also for bone-anchored hearing aids as well as cochlear implant-type hearing aids.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range.

When utilized in a cochlear hearing aid, the first temperature sensor may be arranged to be placed in the ear canal and connected to the behind-the-ear part via a connecting member in a similar way as in either a RITE or BTE hearing aid configuration.

Generally, the present disclosure relates to a hearing aid, a hearing aid system, a binaural hearing aid system and a method.

FIG. 1 illustrates a hearing aid device 10 having a temperature sensor in the in-the-ear part, here illustrated with a dome attached to the housing. A reference, temperature, sensor is included in the behind-the-ear housing. The hearing aid 10 comprises a first housing, here being the in the in-the-ear part, the first housing being configured to be positioned at least partly in the ear canal of the user. An output transducer is also arranged in the first housing, so that the output transducer is arranged in the ear canal of the user during use of the hearing aid. A temperature processor configured to process signals from the first temperature sensor is included in the behind the ear housing. A reference temperature sensor in communication with the temperature processor is also arranged in the housing. The temperature processor is configured to estimate, based on both the first measure body temperature of the user and the reference temperature, a core body temperature of the user.

The hearing aid may, as described elsewhere, be configured in a number of ways, where the common feature is that a temperature sensor is included, and that this temperature sensor preferably is to be arranged as close to the ear drum as possible.

One particular application is hearing aid devices where a receiver/speaker is placed in the ear canal in close proximity to the temperature sensing element. Furthermore, a temperature sensor behind the ear is advantageous.

To obtain a reliable and accurate measurement of body core temperature, the present disclosure provides a combined hard- and software solution. The present disclosure utilizes additional sensor inputs and signal processing to correct for external factors influencing the measurement of the core body temperature of the user.

The temperature from behind-the-ear sensor, or reference sensor, is used to correct for variations in e.g. ambient temperature, as there will be a thermal energy conduction through the wires connecting the in-ear sensor and any hardware positioned behind the ear, i.e. behind the pinna, and radiated heat in and out of the ear canal, which all will influence measurements.

Similarly, movement of the user, like walking and/or running, will increase convection, where accelerometer data can be used to increase reliability in these cases. Such information may be handled similarly to ambient temperature information/data. Also, wind will have similar effect, but may be harder to compensate for as movement is not necessarily detected. Some sensor such as a microphone may however be used to detect these cases. As an example, the microphones of the hearing aid may be used.

The amount of energy being dissipated in the receiver, i.e. the output transducer of the hearing aid, which may also depend on acoustical environment and fitting profile, including receiver and dome model, may be estimated from the mentioned parameters and used for compensation. Such a parameter could be power consumption of the receiver.

The solution is thought to produce superior results and comfort relative to the currently known solutions, which usually occlude the ear to provide a uniform environment for the measurement and then use a simple (non-intelligent) calibration for mapping measured temperature to a correct body core temperature.

Figure 2:
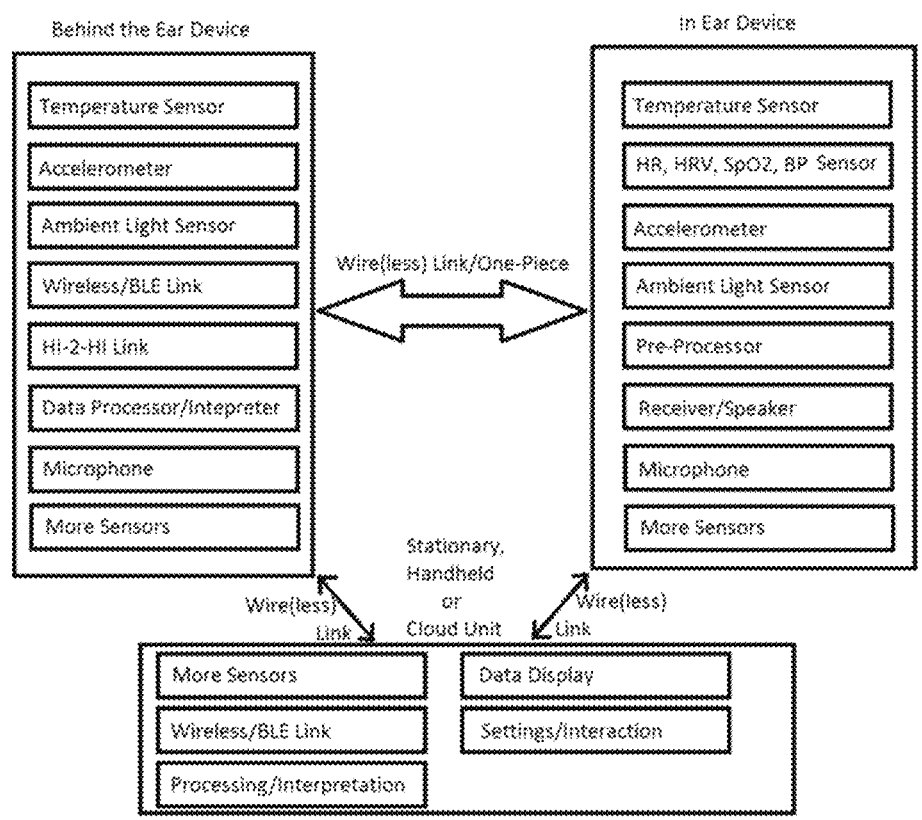
FIG. 2 schematically illustrates sensors.

FIG. 2 schematically illustrates a number of possible sensors and sensor combinations.

Generally, data used in the method may be aggregated over time, or in other ways preprocessed, e.g. to reduce variations. A lowpass filter-type processing may be used to smooth data. Further, data from a time period, e.g. just prior to the calculation/estimation, may be used, so that the corrected estimate is based on more than only the instant measurement of the additional data.

In some implementations of the hearing aid according to the present disclosure, parts of the system may be absent, such as the receiver (in a BTE implementation), temperature sensor behind the ear or similar.

The method described herein will also be applicable to ITE-style hearing aids, where the 'ambient temperature' estimate produced from the sensor behind the ear is placed inside the e.g. on the faceplate of the custom instrument, and thus not as such external to the ear, but at least in a distance from the first temperature sensor.

Information, or data, about ambient temperature can be gathered from external devices instead of using a temperature sensor positioned behind the ear of the user. This could include auxiliary devices, such as a microphone device configured to be positioned at a table and/or on another person whom the user intends to hear better. Also, temperature may be obtained from internet enabled devices, e.g. thermometers with IoT capabilities.

The hearing aid and method according to the present disclosure could utilize additional sensor inputs, such as heart rate (variability), oxygenation, accelerometer, microphones or ambient light sensing to improve reliability by providing more inputs to the algorithm. E.g. detecting physical activity, movement, wind or sunlight.

Many hearing aid users wear a hearing device in each ear, this is usually referred to as a binaural hearing aid. Utilizing setup where a hearing aid device is placed in each ear could be used to increase accuracy and/or scenario detection. One example is the statistical improvement of accuracy obtained by having two independent sensor systems. Another example is if at one ear heating is detected via the behind the ear temperature sensor, while the other does not register such an increase. This could indicate sunlight coming from one side. Wind detected at one side would have a similar effect, albeit cooling and not heating the reference temperature sensor. Thus, a binaural system setup could be used to detect steady state scenarios with high quality data.

Depending on the number of inputs to the compensation algorithm and implementation the processing can be quite computationally intensive. In a small, battery powered device like a hearing aid device, reducing processing requirements may be important for battery life extension. Offloading processing to another device, such as a smartphone, wearable and/or a cloud server may increase power efficiency of the hearing aid device and leave more processing power for latency sensitive algorithms running on the hearing aid device.

The method as disclosed herein is not limited to hearing aid device sensors, but could include inputs from other sensors found in devices such as phones, e.g. location sensors (GPS), statically located devices, e.g. weather stations, or other wearables (e.g. Smartwatches) becoming increasingly available.

The part of the hearing instrument including the in-ear temperature sensor could include a memory device so that the hearing aid is able to determine, based on identification information stored in the memory device, exactly which sensor or sensors are present in the device. This information may then be provided to the processor which then may determine if some sensor data should be given more weight in the compensation due to higher accuracy. It will also serve as s simpler way to detect sensors in-stead of requiring fixed addresses on a digital bus for each sensor and/or sensor type.

Figure 3:
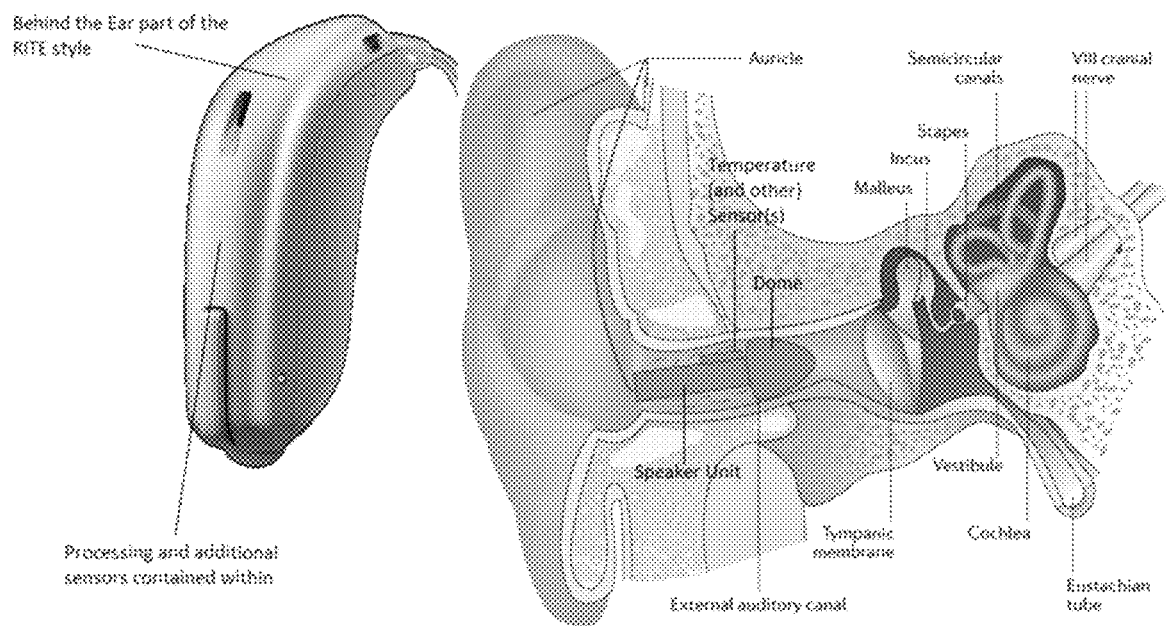
FIG. 3 schematically illustrates a hearing aid on an ear.

FIG. 3 schematically illustrates positioning of a in-the-ear part with a temperature sensor.

Figure 4:
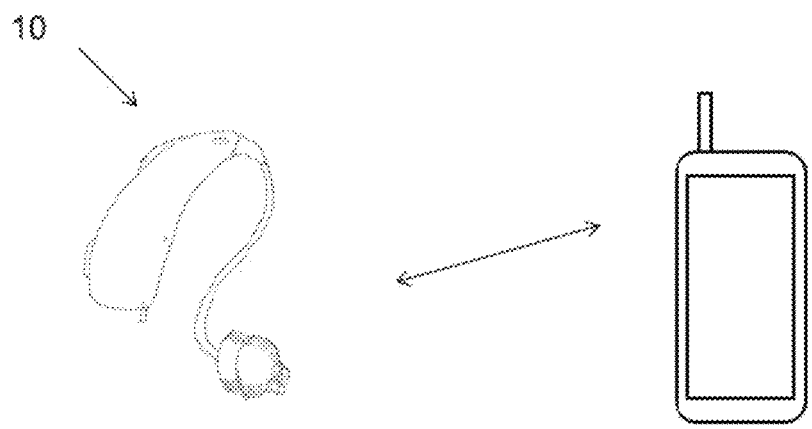
FIG. 4 schematically illustrates a hearing aid and a phone.

FIG. 4 schematically illustrates a hearing aid in wireless communication with a smartphone.

Figure 5:
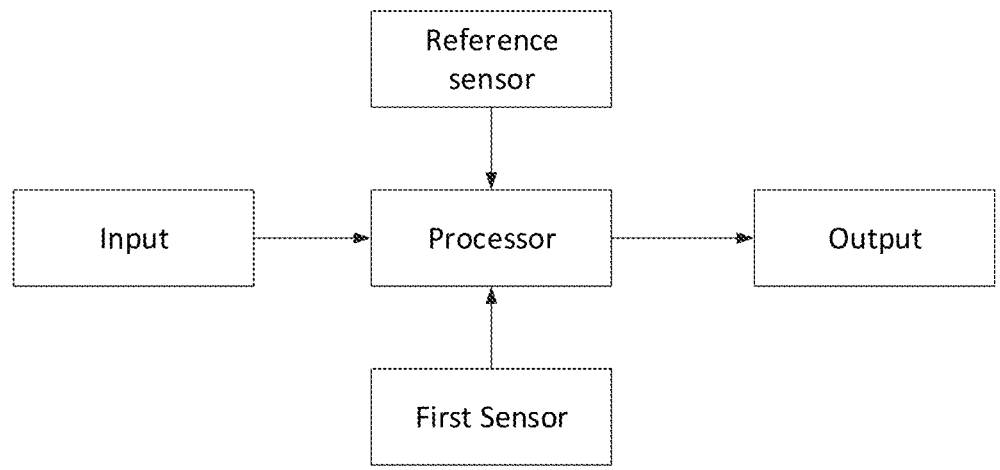
FIG. 5-9 schematically illustrates various arrangements of hearing aid components, and FIG. 10 schematically illustrates steps of a method.

FIG. 5 schematically illustrates components of a hearing aid with a first sensor and a reference sensor.

Figure 6:
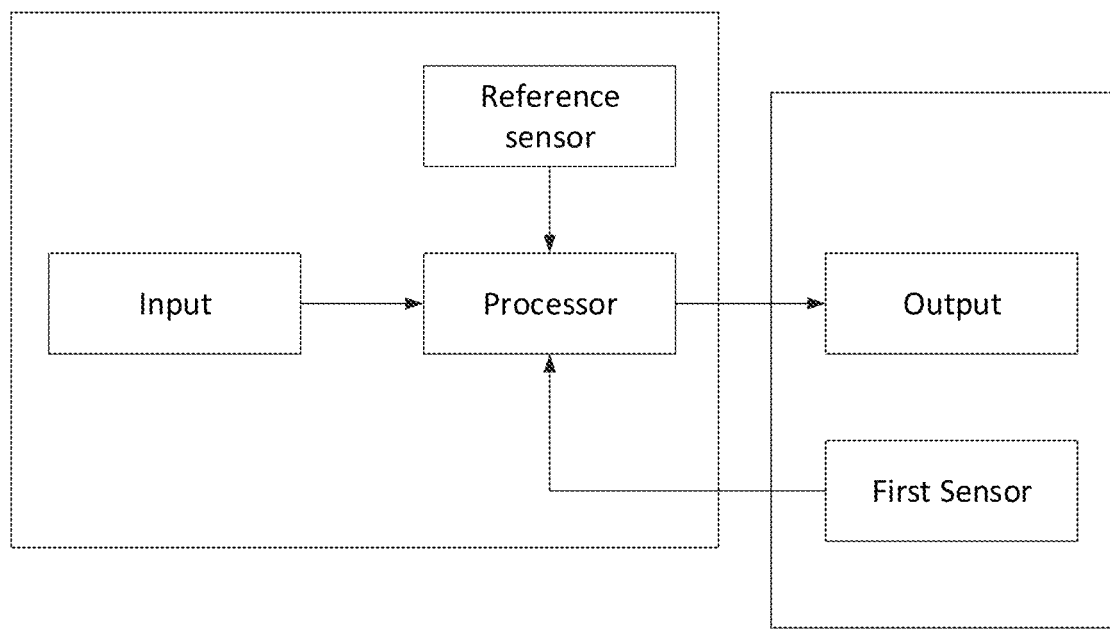

FIG. 6 schematically illustrates components of a hearing aid with a first sensor and a reference sensor, where the first sensor and the output transducer are arranged in a housing separate from the housing having the input transducer, the reference sensor and the processor.

Figure 7:
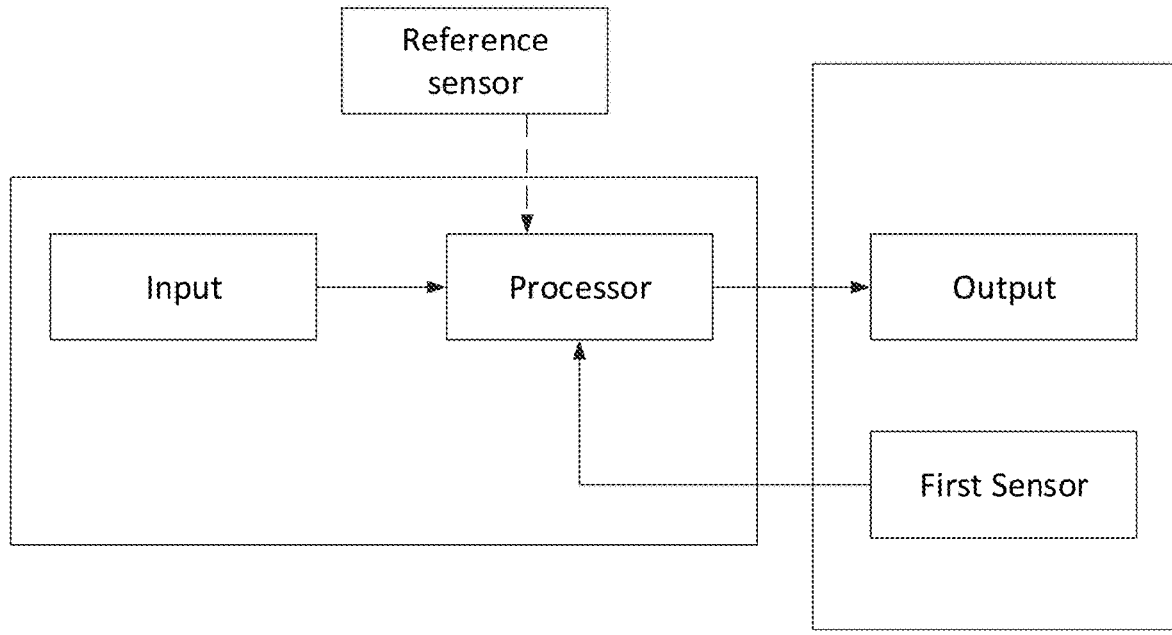

FIG. 7 schematically illustrates components of a hearing aid with a first sensor and a reference sensor, where the first sensor and the output transducer are arranged in a housing separate from the housing having the input transducer and the processor. The reference sensor is in a third housing and in communication with the processor.

Figure 8:
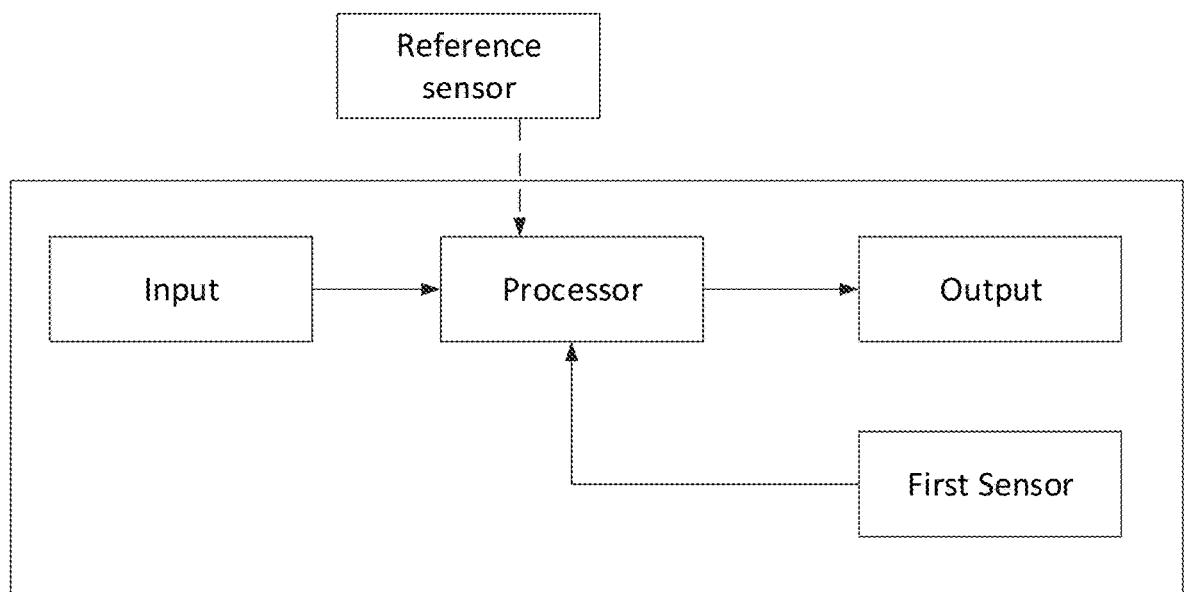

FIG. 8 schematically illustrates components of a hearing aid with a first sensor and a reference sensor, where the first sensor, the output transducer, the input transducer and the processor are arranged in a housing separate from the housing having the reference sensor.

Figure 9:
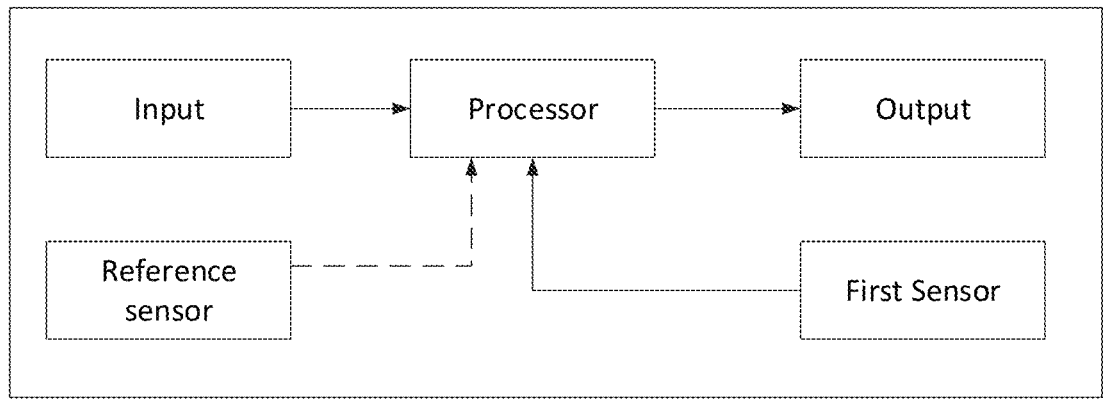

FIG. 9 schematically illustrates components of a hearing aid where all components are included in the same housing.

Figure 10:
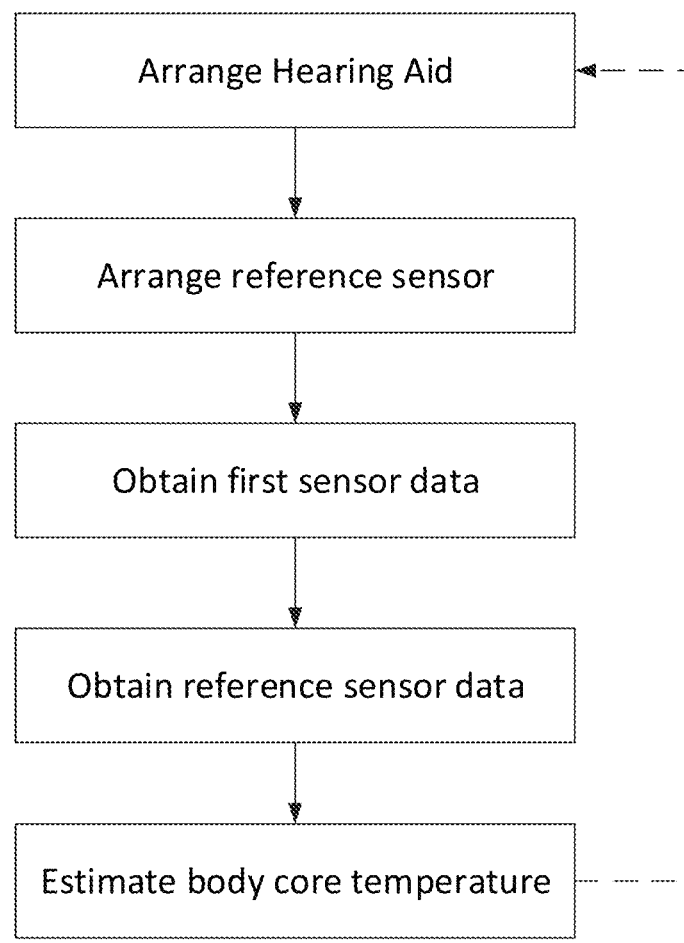

FIG. 10 schematically illustrates steps of a method according to the present disclosure.

In an aspect, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

In an aspect, a data processing system comprising a processor adapted to execute the computer program for causing the processor to perform at least some (such as a majority or all) of the steps of the method described above and in the claims.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A hearing aid having a first housing, the first housing being configured to be positioned at least partly in an ear canal of a user,
   a first temperature sensor arranged in the first housing,
   an output transducer arranged in the first housing,
   a temperature processor configured to process signals from the first temperature sensor,
   a reference temperature sensor in communication with the temperature processor, and
   a motion sensor configured to provide an indication of movement of the hearing aid representing movement, wherein
   the temperature processor includes movement of the hearing aid as a measure of movement of the user when estimating the core body temperature of the user, and
   the temperature processor is configured to estimate, based on both the first measure body temperature of the user and the reference temperature, a core body temperature of the user.

2. The hearing aid according to claim 1, wherein the temperature processor is further configured to provide the estimate based on an amount of output transducer activity to compensate for the local heating of the temperature sensor originating from heat produced by the output transducer.

3. The hearing aid according to claim 1, wherein first housing comprises a first end and an opposite second end, wherein the first temperature sensor is arranged in the first end of the first housing and the output transducer is arranged at an extreme end of the opposite second end.

4. The hearing aid according to claim 1, wherein the hearing aid further comprises a second housing, the reference temperature sensor being arranged in the second housing.

5. The hearing aid according to claim 4, wherein the second housing is configured to be positioned behind the ear of the user, or wherein the second housing is configured to be positioned in the concha of the user and/or the fossa triangularis.

6. The hearing aid according to claim 1, wherein the reference temperature sensor is arranged in an external device in wired or wireless communication with the temperature processor.

7. The hearing aid according to claim 6, wherein the external device is a telephone device or an auxiliary device having a microphone array.

8. The hearing aid according to claim 1, wherein the motion sensor is or includes an accelerometer.

9. The hearing aid according to claim 1, wherein the hearing aid further comprises a secondary sensor configured to obtain a measure indicative of wind at the hearing aid, and the temperature processor includes wind measure at the hearing aid when estimating the core body temperature of the user.

10. A method of obtaining an estimate of the core body temperature of a user, wherein a hearing aid comprising a first housing configured to be positioned at least partly in thcan ear canal of the user, the first housing including a first temperature sensor, a temperature processor configured to process signals from the first temperature sensor, a reference temperature sensor in communication with the temperature processor, wherein the hearing aid further comprises a motion sensor configured to provide an indication of movement of the hearing aid, the method including:
    arranging the first housing in or at the ear canal of the user so that the first temperature sensor is in the ear canal of the user, the reference temperature sensor being arranged outside the ear canal of the user,
    obtaining from the first temperature sensor a first measure of body temperature of the user,
    obtaining data relating to movement of the hearing aid as a measure of movement of the user,
    obtaining a reference temperature from the reference temperature sensor, and
    estimating, based on both the first measure body temperature of the user, the reference temperature and the data relating to movement of the hearing aid, a core body temperature of the user.

11. The method according to claim 10, wherein the first housing further comprises an output transducer, and the method further comprises a step of:
    compensating for local heating of the temperature sensor originating from heat produced by the output transducer during output transducer activity when estimating the core body temperature.

12. The method according to claim 10, wherein the reference temperature sensor is arranged in an external device in wired or wireless communication with the temperature processor, and the method further comprises a step of:
    communicating the reference temperature wired or wirelessly from the external device to the temperature processor.

13. The method according to claim 10, wherein the hearing aid further comprises a secondary sensor configured to obtain a measure indicative of wind at the hearing aid, and the method includes a step of obtaining data relating to wind measure at the hearing aid, and
    the step of estimating the core body temperature of the user includes the data relating to wind measure.

* * * * *